United States Patent [19]
Walker

[11] Patent Number: 5,399,762
[45] Date of Patent: Mar. 21, 1995

[54] QUATERNARY AMMONIUM HYDROXIDE COMPOSITIONS AND PREPARATION THEREOF

[75] Inventor: Leigh E. Walker, Macungie, Pa.

[73] Assignee: Lonza, Inc., Annandale, N.J.

[21] Appl. No.: 74,313

[22] Filed: Jun. 9, 1993

[51] Int. Cl.⁶ .......................................... C07C 209/68
[52] U.S. Cl. .................................... 564/296; 564/282; 564/291
[58] Field of Search ........................ 564/282, 291, 296

[56] References Cited

U.S. PATENT DOCUMENTS

| | | | |
|---|---|---|---|
| 2,994,699 | 8/1961 | De Benneville | 260/294.7 |
| 3,169,983 | 2/1965 | Hunter | 260/462 |
| 3,233,645 | 12/1965 | Kalberg | 252/117 |
| 3,281,458 | 10/1966 | Jordan et al. | 260/501 |
| 3,301,815 | 1/1967 | Hunyar et al. | 260/45.9 |
| 3,646,147 | 2/1972 | Dadekian | 260/583 R |
| 4,216,168 | 8/1980 | Evans et al. | 564/296 |
| 4,585,795 | 4/1986 | Linderborg | 514/558 |
| 4,929,454 | 5/1990 | Findlay | 424/638 |
| 5,004,760 | 4/1991 | Patton et al. | 521/149 |

FOREIGN PATENT DOCUMENTS

| | | |
|---|---|---|
| 0293192 | 5/1988 | European Pat. Off. . |
| 1518427 | 3/1968 | France . |
| 618433 | 2/1949 | United Kingdom . |
| 650304 | 2/1951 | United Kingdom . |
| 669506 | 4/1952 | United Kingdom . |
| 719617 | 12/1954 | United Kingdom . |
| 795814 | 5/1958 | United Kingdom . |

OTHER PUBLICATIONS

Whitten et al. *General Chemistry* Saunders College Publishing, New York, (1981) p. 334.

D. D. Nicholas et al., "Distribution and Permanency of DDAC in Southern Pine Sapwood Treated by the Full-Cell Process", *Forest Products Journal* 41 (1):41–45 (Jan. 1991).

L. Jin & A. F. Preston, "The Interaction of Wood Preservatives With Lignocellulosic Substrates" *Holzforschung* 45 (6):455–459.

*Proc. Amer. Wood-Preservers Assoc.* 80:191–209 (1984).

Y. Nakama, F. Harusawa & I. Murotani, "Cloud Point Phenomena In Mixtures of Anionic and Cationic Surfactants in Aqueous Solution" *JAOCS* 67 (11):717–721, (Nov. 1990).

A. F. Preston et al., "Recent Research On Alkylammonium Compounds In The U.S.", *American Wood-Preservers' Association*, 83:331–348 (1987).

"Quaternary Ammonium Compounds, Fine & Functional Chemicals" *AKZO*, pp. 1, 3–20 (1991).

D. D. Miller et al., "Control of Aggregate Structure With Mixed Counterions In An Ionic Double-Chained Surfactant", *Langmuir* 4(6):1363–1367 (1988).

Ewa Z. Radlinska et al., "Supra-Self Assembly: Vesicle-Micelle Equilibrium", *Colloids and Surfaces* 46:213–217 (1990).

J. E. Brady et al., "Counterion Specificity As The Determinant of Surfactant Aggregation" *J. Phys. Chem.* 90:1853–1859, (1986).

D. D. Miller et al., "Fluorescence Quenching In Double-Chained Surfactants. 1. Theory of Quenching In Micelles and Vesicles" *J. Phys. Chem.* 93:323–325 (1989).

J. E. Brady et al., "Spontaneous Vesicles", *J. American Chemical Society* 106:4279–4280 (1984).

A. F. Preston, "Dialkyldimethylammonium Halides As Wood Preservatives", *JAOCS* 60 (3):567–570 (Mar. 1983).

(List continued on next page.)

*Primary Examiner*—Peter O'Sullivan
*Attorney, Agent, or Firm*—Darby & Darby

[57] ABSTRACT

A high yield method for the preparation of $C_1$–$C_{20}$ alkyl or aryl-substituted alkyl, $C_8$–$C_{16}$ alkyl quaternary ammonium-hydroxide is provided whereby two reactants, a corresponding quaternary ammonium chloride and a metal hydroxide, are reacted in a solvent comprising a $C_1$–$C_4$ normal alcohol. The amount of metal hydroxide reactant is that amount sufficient to yield the quaternary ammonium hydroxide and a metal chloride.

Also provided are wood preservative systems which include (a) a biocidal effective amount of at least one di $C_8$–$C_{12}$ alkyl quaternary ammonium hydroxide and (b) a solvent, as well as a method for preserving a wood substrate whereby the substrate is treated with the preservative system.

15 Claims, 2 Drawing Sheets

OTHER PUBLICATIONS

D. D. Nicholas & A. F. Preston, "Interaction of Preservatives With Wood" *Chemistry of Solid Wood*, pp. 307–320 (1984).

E. W. Anacker and H. M. Ghose, "Counterions and Micelle Size I. Light Scattering by Solutions of Dodecyltrimethylammonium Salts", vol. 67 pp. 1713–1715, (Aug. 1963).

L. Sepulveda et al., "A New and Rapid Method for Preparing Long-Chain Alkyltrimethylammonium Salts With A Variety of Counterions", *Journal of Colloid and Interface Science* 117 (2):460–463 (Jun. 1987).

E. Jugerman et al., *Cationic Surfactants*, pp. 56–57, Marcel Dekker Inc. (1969).

"Quaternary Ammonium Compounds", *K.O.* 19:521–531 (1982).

"Quaternary Ammonium Compounds", *K.O.* 16:859–865 (1968).

Astle, "Industrial Organic Nitrogen Compounds", Reinhold Publ. pp. 64–67 (1961).

"Organic Reactions" 11, Chaptr. 5, Krieger Publ. Co., pp. 376–383 (1960).

Carl Kaiser et al., "Alkenes via Hofmann Elimination: Use of Ion-Exchange Resin For Preparation Of Quaternary Ammonium Hydroxides: Diphenylmethyl Vinyl Ether", *Organic Synthesis*, Collective vol. VI, pp. 552–554, John Wiley, Inc. (1988).

Y. Talmon et al., "Spontaneous Vesicle Formed From Hydroxide Surfactants: Evidence From Electron Microscopy" *Science* 221:1047–1048 (Sep. 9, 1983).

Awata et al., "Cathodic Esterification of Carboxylic Acids", *Chemistry Letters*, pp. 371–374 (1985).

A. W. Ralston et al., "The Solubilities of Long-Chain Dialkyldimethyl-Ammonium Chlorides In Organic Solvents", Contribution from the Research Laboratory of Armour and Company 13:186–190 (1948).

A. W. Ralston et al., "Conductivities of Quaternary Ammonium Chlorides Containing Two Long-Chain Alkyl Groups", Contribution from the Research Laboratory of Armour and Company 70:977–979 (Mar. 1948).

*Organic Chemistry* 35:3597–3598 (1941).

T. P. Schultz et al., "Role of Stilbenes in the Natural Durability of Wood: Fungicidal Structure-Activity Relationships", *PhytoChemistry* 29:1501–1507 (1990).

85: 123253x "A Simple Preparation of Anhydrous Tetraalkylammonium Salts" (Chem. Abstract) (1976).

115: 87485b "Wood Preservatives Containing Quaternary Ammonium Salts With Polymers" (Chem. Abstract) (1991).

112: 212470j "Agrochemical Fungicides Containing Quaternary Ammonium Salts" (Chem. Abstract) (1990).

113:153776j "Microbicidal Thermoplastic Resin Compositions" (Chem. Abstract) (1990).

112: 79768u "Noncorrosive Quaternary Ammonium Compounds As Wood Preservatives" (Chem. Abstract) (1990).

113: 163999y "Capacitor Driving Electrolytes and Their Preparation" (Chem. Abstract) (1990).

112: 54969x "Preparation of Quaternary Ammonium Hydroxides Free of Halogens" (Chem. Abstract) (1990).

110: 212114e "Process For Producing Quaternary Salts" (Chem. Abstract) (1989).

114: 246824j "Preparation of Carbonic Half-Esters of Betaine Structure" (Chem. Abstract) (1991).

98: 200032x "Didecyldimethylammonium Chloride-A Quaternary Ammonium Wood Preservative" (Chem. Abstract) (1983).

91: 152627b "Efficacy of Acidic and Alkaline Solutions of Alkylammonium Compounds As Wood Preservatives" (Chem. Abstract) (1979).

113: 154360f "Microbicidal Coating Compositions Containing Quaternary Ammonium Salts" (Chem. Abstract) (1990).

109: 124403x "Quaternary Ammonium Salt-Containing Wood Preservatives" (Chem. Abstract) (1988).

103: 109954k "Clear Aqueous Disinfectant Solutions Containing Chlorhexidine Lactate Or Gluconate And Quaternary Ammonium Salts" (Chem. Abstract) (1985).

70: 111034d "Quarternary Ammonium Bases Compatible With Scintillation-Counting Liquids" (Chem. Abstract) (1969).

60: 16447d "Nematocidal Quaternary Ammonium Salts" (Chem. Abstract) (1964).

91: 109311g "Composition For Removing Water From Surfaces of Articles" (Chem. Abstract) (1979).

75: 119170u "Corrosion-Resistant Lubricants and Antistatic Agents" (Chem. Abstract) (1971).

66: 66227y "Stabilization of Vinyl Resins With Organic Quaternary Ammonium Nitrates" (Chem. Abstract) (1967).

66: 1953n "N-Alkyl Ammonium Humates" (Chem. Abstract) (1967).

97: 91725g "Perfluoroalkyl Alkanols" (Chem. Abstract) (1982).

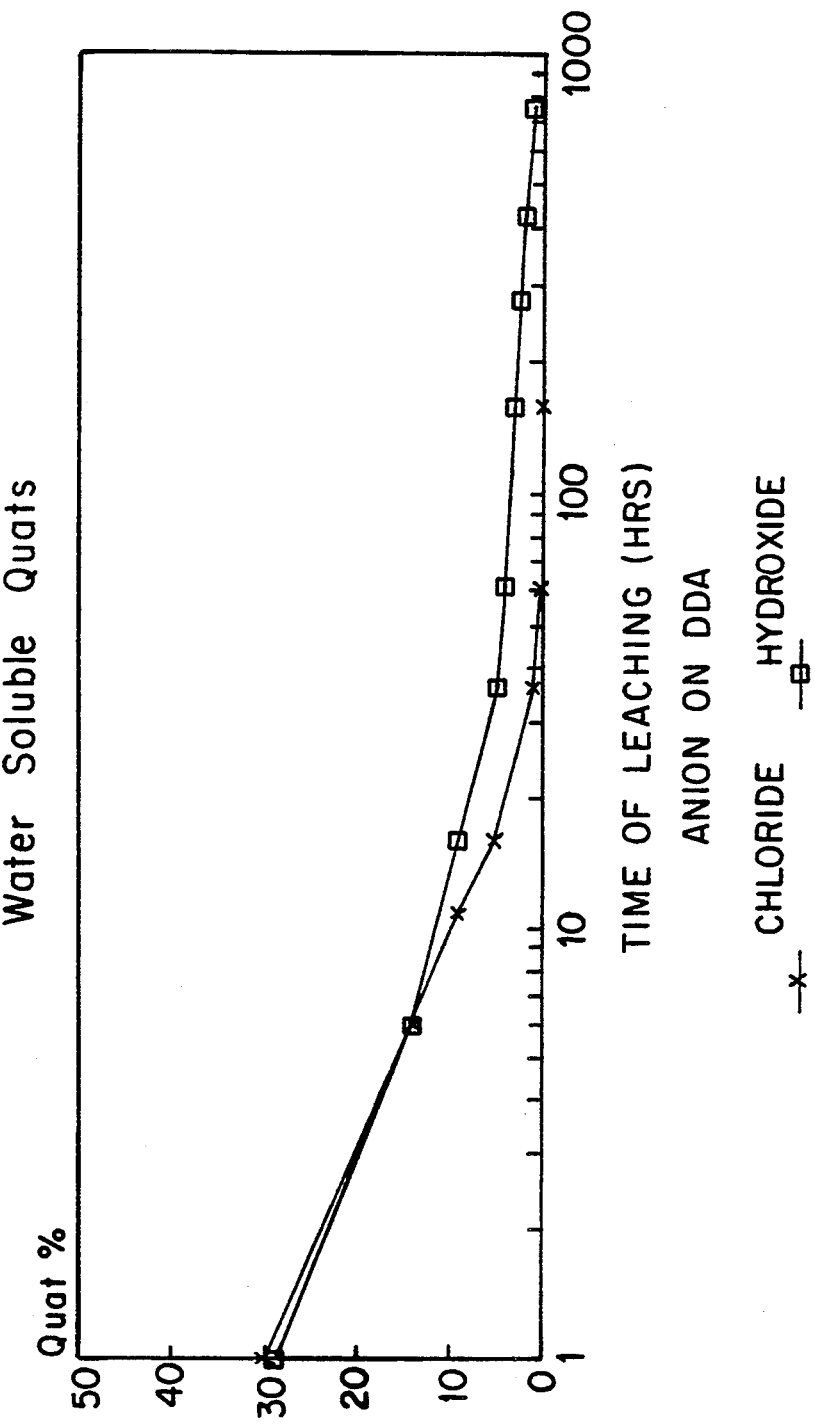

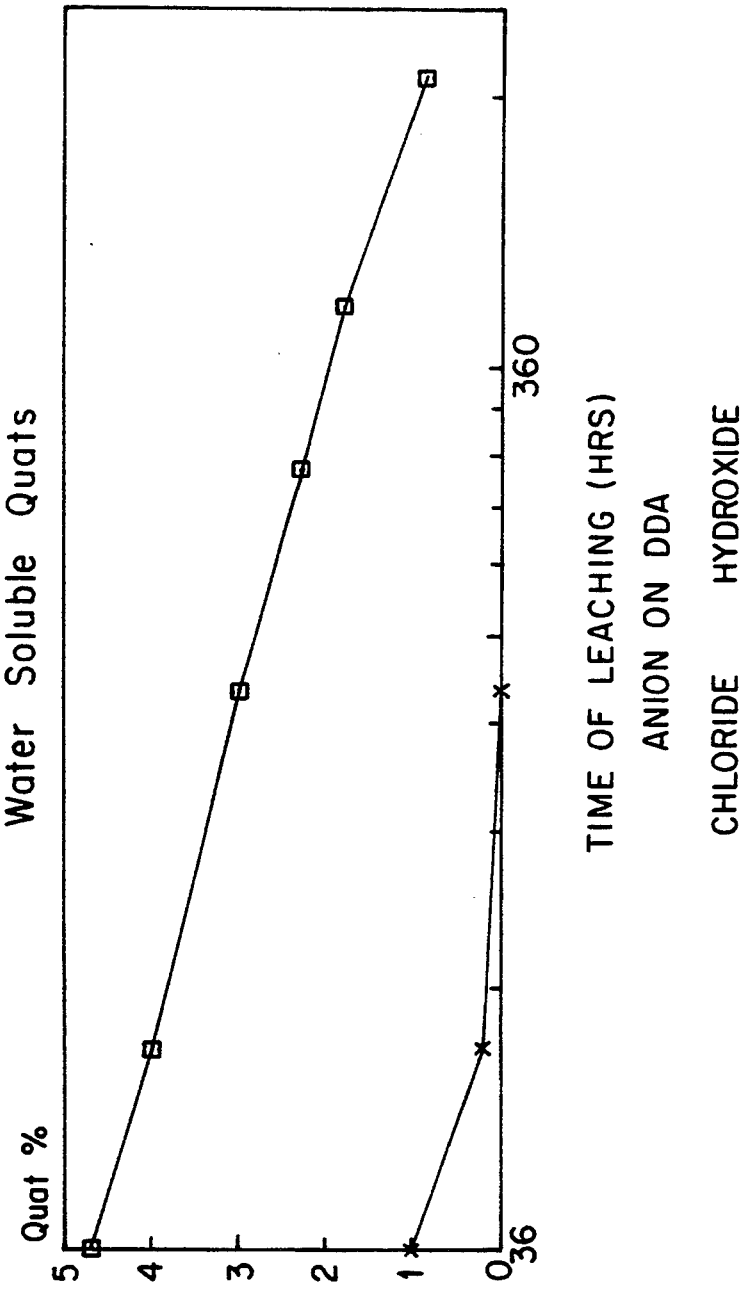

QUATERNARY AMMONIUM HYDROXIDE COMPOSITIONS AND PREPARATION THEREOF

| Table of Related Applications | | | | |
|---|---|---|---|---|
| Attorney's Docket No. | Appln. No. | Dated Filed | Title | Inventor |
| 5408/07432 | 08/074,312 | 9 June 1993 | Quaternary Ammonium Carbonate Compositions and Preparation Thereof | Leigh E. Walker |
| 5408/07424 | 08/074,136 | 9 June 1993 | Quaternary Ammonium Carboxylate Compositions and Preparation Thereof | Leigh E. Walker |
| 5408/07426 | 08/074,314 | 9 June 1993 | Waterproofing and Preservative Compositions and Preparation Thereof | Leigh E. Walker |

FIELD OF THE INVENTION

This invention relates to the preparation of $C_1$–$C_{20}$ alkyl or aryl-substituted alkyl, $C_8$–$C_{20}$ alkyl quaternary ammonium hydroxide compositions by an indirect synthesis method which uses a corresponding quaternary ammonium chloride as a starting material. Di $C_8$–$C_{12}$ alkyl quaternary ammonium compositions, preferably prepared according to the method of the present invention, are useful in wood preservative systems, as surfactants, and as biocides. Preferably, these wood preservative systems are metal free.

BACKGROUND OF THE INVENTION

Quaternary ammonium compounds (quats) are typically prepared by the reaction:

$$R^1R^2R^3N + R^4X \rightarrow R^1R^2R^3R^4NX \quad (I)$$

wherein X is a halogen, a sulfate, a sulfo compound, or the like. When at least one of $R^1$, $R^2$, $R^3$, or $R^4$ is $C_{12}$ or longer, the product is an inert soap. Many of the inert soaps have biocidal activity against bacteria, fungi, algae, and related organisms.

Reaction (I) above is limited by the reactant $R^4X$ because $R^4$ must react with tertiary amines. For example, methyl chloride ($R^4X = CH_3Cl$) will react with a tertiary amine at less than 100° C. to yield a quaternary compound $R_3N^+CH_3\ Cl^-$, while methanol or methyl acetate ($R^4X = CH_3OH$ or $CH_3COOCH_3$) will not, under similar reaction conditions.

General quaternary ammonium compounds with a sulfo group are easily prepared either by the reaction of a sulfate compound with a tertiary amine (II) or by a double exchange (III).

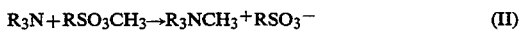

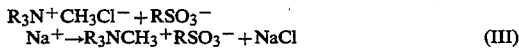

Quaternary ammonium hydroxides (hydroxy quats) are currently prepared by the reaction of quaternary ammonium iodide with silver oxide (IV).

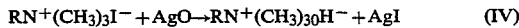

However, this reaction is costly, and it is difficult to recover the silver reagent. See, Organic Reactions, 11:Chptr 5, pp. 376–377, Krieger Publishing Co., 1975.

In an olefin synthesis, it has been suggested to treat a quaternary salt with aqueous sodium or potassium hydroxide followed by pyrolysis in order to form the hydroxy quat and then to decompose the hydroxy quat directly. However, in this method the hydroxy quat is not isolated and the conditions for its preparation are undesirable. See, Organic Reactions, 11:Chptr 5, pp. 376–377, Krieger Publishing Co., 1975.

Talmon et al., Science, 221, 1047 (1983), have used an ion exchange resin to convert didecyldimethylammonium bromide to didecyldimethylammonium hydroxide (V).

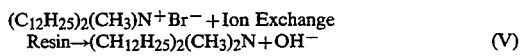

However, 50 ml of ion exchange resin and two treatment steps were required to convert 3 grams of quaternary ammonium chloride to the corresponding hydroxide. See also, Organic Synthesis, Collective Volume VI, 552, John Wiley Inc., 1988; Brady et al. J. Am. Chem. Soc., 106:4280–4282, 1984; Brady et al. J. Phys. Chem., 90:9, 1853–1859, 1986; Miller et al. J. Phys. Chem, 91:1, 323–325, 1989; Radlinske et al. Colloids and Surfaces, 46:213–230, 1990.

Alternatively, quaternary ammonium hydroxide compositions have been prepared by treating a haloquat in an electrochemical cell with special cation exchange diaphragms between the cells. The hydroxy quat collects at one electrode, and the halide collects at the other. See, Japanese Patent Publication No. 02-106,915; Awata et al., Chemistry, Letters, 371 (1985).

Japanese Patent Publication No. 01-172,363 discloses the preparation of relatively low yields of tetraethylammonium hydroxide by reacting triethylamine with diethyl sulfate, heating the resultant quat with sulfuric acid to yield the sulfate quat, and reacting the sulfate quat with barium hydroxide to yield the short chain quat, tetraethylammonium hydroxide, and barium sulfate.

Di $C_8$–$C_{12}$ alkyl quaternary ammonium hydroxides prepared by ion exchange were used as strong bases to digest animal tissue by Bush et al., French Patent Publication No. 1,518,427.

Akzo discloses that the addition of a metallic hydroxide to a quaternary ammonium chloride such as didecyldimethylammonium chloride, in an aqueous medium, results in an equilibrium mixture of quaternary ammonium chloride and quaternary ammonium hydroxide (VI). This reaction can be driven to the right by the use of isopropanol as a solvent.

Quaternary ammonium compounds (quats) and particularly didecyldimethylammonium chloride (DDAC)

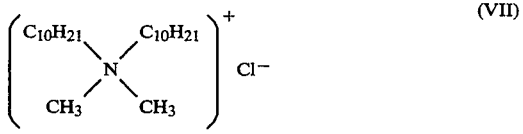

(VII)

could be used as wood preservatives if they were stable because they possess resistance properties to fungi and termites, to loss of strength, and to electrical sensitivity similar to those of commonly used acidic copper/chromium/arsenic solution (CCA) or ammoniacal copper and arsenic salt solution preservatives. See *Proc of the Am. Wood Pres. ASSOC.*, 80:191–210 (1984). Although chloride quats do not include potentially dangerous heavy metals, didecyldimethylammonium chloride leaches rapidly in soil (Nicholas et al., *Forest Prod. J.*, 41:41 (1991), and therefore, does require coupling with copper salt.

Findlay et al., U.S. Pat. No. 4,929,454, disclose a method of preserving wood by impregnation with a quaternary ammonium compound and at least one of zinc and copper, wherein the quat anion is chosen from the group consisting of hydroxide, chloride, bromide, nitrate, bisulfate, acetate, bicarbonate, and carbonate, formate, borate and fatty acids. These quats have distinct environmental and safety advantages over commonly used acidic copper/chromium/arsenic solution (CCA) or ammoniacal copper and arsenic salt solution preservatives in that potentially dangerous heavy metals are not included. The Findlay et al. quats require copper or zinc in order to render them relatively insoluble and to prevent them from leaching out of a treated substrate. The use of copper or zinc in the above formulations may yet raise environmental and corrosion concerns.

Additionally, didecyldimethylammonium chloride tends to absorb preferentially to the surface of the wood and does not uniformly treat the whole substrate. Finally, DDAC treated wood shows surface erosion or ages upon exposure to light. See Preston et al., *Proc. Am. Wood Pres. Assoc.*, 83:331 (1987).

The biocidal activities of various chloride quats against bacteria, fungi, and algae are tabulated in *Cationic Surfactants*, E. Jungerman Ed., pp. 56–57, Marcel Dekker, Inc., 1969. Nicholas, "Interaction of Preservatives with Wood", *Chemistry of Solid Wood*, Advance in Chemistry Series #207, Powell ed., (A.C.S. 1984) notes that didecyldimethylammonium compounds and particularly DDAC are potential biocides. Preston, J.A-.O.C.S. 60:567 (1983) concurs and suggests that maximum fungitoxicity is exhibited with dialkyldimethyl compounds having $C_{10}$–$C_{12}$ alkyl groups. Butcher et al., Chem Abstracts No. 91:152627b, suggests that the presence of an acid or a base can affect the activity of didecyldimethylammonium quats.

Consequently, efforts have been directed to develop a safe, efficient and expedient method to prepare quaternary ammonium compounds that do not require potentially hazardous metal additives to treat wooden substrates effectively.

DESCRIPTION OF THE DRAWINGS

FIG. 1A is a graphic comparison of leaching of a wood preservative system according to the present invention and a wood preservative system of the prior art.

FIG. 1B is an enlarged segment of the graph of FIG. 1A.

SUMMARY OF THE INVENTION

A high yield method for the preparation of $C_1$–$C_{20}$ alkyl or aryl-substituted alkyl, $C_8$–$C_{20}$ alkyl quaternary ammonium hydroxide, and preferably di $C_8$–$C_{12}$ alkyl quaternary ammonium hydroxide, which includes the selection of particular solvents, has been discovered. Product yield can be further enhanced by adjustment of the amounts of the reactants. These hydroxy quats and wood preservative compositions prepared therefrom can be applied to wood substrates with relatively insignificant leaching from the substrate.

The method of the present invention comprises reacting two reactants, a $C_1$–$C_{20}$ alkyl or aryl-substituted alkyl, $C_8$–$C_{20}$ alkyl quaternary ammonium chloride, preferably a di $C_8$–$C_{12}$ alkyl quaternary ammonium chloride, and a metal hydroxide, in a solvent comprising a $C_1$–$C_4$ normal alcohol. The amount of metal hydroxide reactant is that amount sufficient to yield the $C_1$–$C_{20}$ alkyl or aryl-substituted alkyl, $C_8$–$C_{20}$ alkyl quaternary ammonium hydroxide and a metal chloride. Preferably, this amount is at least a stoichiometric amount.

Also contemplated by the invention are wood preservative systems that preferably are metal-free and which include a biocidal effective amount of at least one di $C_8$–$C_{12}$ alkyl ammonium hydroxide and a solvent. Preferably, the di $C_8$–$C_{12}$ alkyl quaternary ammonium hydroxide is prepared by the method above.

Further contemplated by the invention is a method for preserving a wood substrate. Accordingly, the substrate is treated with a these wood preservative systems.

DETAILED DESCRIPTION OF THE INVENTION

The method of the present invention provides increased yields of $C_1$–$C_{20}$ alkyl or aryl-substituted alkyl, $C_8$–$C_{20}$ alkyl quaternary ammonium hydroxide, and preferably di $C_8$–$C_{12}$ alkyl quaternary ammonium hydroxide, when compared with conventional production methods. Although it was previously believed that the reaction of the chloride quat salt with a metal hydroxide to yield quaternary ammonium hydroxide and metal chloride was an equilibrium reaction (VII) or could be driven to the right by the use of branched solvents, it has now been discovered that by selection of the proper reactants, reaction medium, and/or reaction conditions (including reactant amounts), the reaction can be driven well past equilibrium to yield unprecedented greater amounts of $C_1$–$C_{20}$ alkyl or aryl-substituted alkyl, $C_8$–$C_{20}$ alkyl quaternary ammonium hydroxide.

Although the present method can be used to prepare a variety of $C_1$–$C_{20}$ alkyl or aryl-substituted alkyl, $C_8$–$C_{20}$ alkyl quaternary ammonium hydroxide compounds, the preferred reaction product quat is a di $C_8$–$C_{12}$ alkyl quaternary ammonium hydroxide compound. Most preferred hydroxy quats are di n-$C_8$–$C_{12}$ alkyl quaternary ammonium hydroxide, didecyldimethylammonium hydroxide, and di-n-decyldimethylammonium hydroxide.

Didecyldimethylammonium hydroxide, when observed in a 70 to 80 percent by weight solution in a 50 percent by weight alcohol/50 percent by weight water solvent, is a yellow/orange liquid. This formulation has a flash point of about 134° F., and it is a highly alkaline material that reacts with the phenolic OH of lignin.

The reaction is illustrated below.

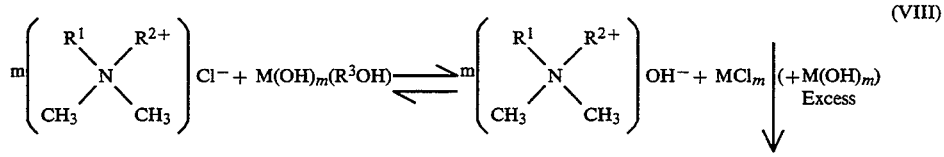

wherein $R^1$ is a $C_1$–$C_{20}$ alkyl or aryl-substituted alkyl group; $R^2$ is a $C_8$–$C_{20}$ alkyl group; $R^3$ is a straight chain $C_1$–$C_4$ alkyl group; M is a mono-, di-, or trivalent metal; and m is one if M is monovalent, two if M is divalent, and three if M is trivalent. Preferably $R^1$ is the same as $R^2$, i.e. a $C_8$–$C_{12}$ alkyl group.

Many $C_1$–$C_{20}$ alkyl or aryl-substituted alkyl, $C_8$–$C_{20}$ alkyl quaternary ammonium chlorides are suitable reactants, but di $C_8$–$C_{12}$ alkyl quaternary ammonium chloride is preferred, and didecyldimethylammonium chloride, and particularly, di-n-decyldimethylammonium chloride are most preferred. The selections of the $R^1$ and $R^2$ substituents of the chloride quat reactant are determinative of the hydroxy quat product.

Special mention is also made of processes wherein $R^1$ is a methyl, butyl, $C_8$ alkyl, $C_9$ isoalkyl, $C_{10}$ alkyl, $C_{12}$ alkyl, $C_{14}$ alkyl or benzyl group; and $R^2$ is a $C_{10}$ alkyl, $C_{12}$ alkyl, $C_{14}$ alkyl or $C_{16}$ alkyl group.

The metal hydroxide reactant is a mono-, bi-, or trivalent metal, preferably a monovalent metal hydroxide, and most preferably an alkali metal hydroxide such as sodium hydroxide or potassium hydroxide. Special mention is made of potassium hydroxide. The metal chloride reaction product will precipitate and is easily removed, i.e. by filtration or the like, yielding a hydroxy quat/solvent reaction product. The hydroxy quat can be separated therefrom by drying or the like.

The reaction is conducted in a solvent which comprises a $C_1$–$C_4$ normal alcohol. Preferably, the solvent is ethanol, and most preferably, anhydrous ethanol.

The amount of metal hydroxide reactant typically is a stoichiometric amount with respect to the quaternary ammonium chloride reactant. Therefore, on a theoretical basis and if the reaction were complete and unequilibrated, there would be no excess of metal hydroxide reactant upon completion of the reaction. In practice, yield when using a stoichiometric amount of metal hydroxide reactant will range from about 65% to about 95%, but will vary, dependent in part upon the particular metal hydroxide reactant.

Yield can be further improved over conventional methods by utilization of a stoichiometric excess of metal hydroxide ranging from about 2% to about 20% excess. If an excess of metal hydroxide is used, yield will be increased to from about 95% to about 99%, again varying as above.

The unreacted metal hydroxide is soluble in the hydroxy quat/solvent mixture. Any excess or unreacted metal hydroxide should be removed after the reaction is completed, and is preferably precipitated by subsequent reaction with carbon dioxide to yield the corresponding metal carbonate. The carbonate is insoluble in the hydroxy quat/solvent mixture and is easily removed, i.e. by filtration or the like. Alternatively, a solid metal bicarbonate, in which the metal corresponds to the metal of the metal hydroxide, can be added and slurried with the hydroxy quat/solvent mixture. The soluble metal hydroxide reacts with solid bicarbonate to yield the insoluble metal carbonate. The metal carbonate does not react further with the hydroxy quat.

Mixing, adding, and reacting of the components in the method of the present invention can be accomplished by conventional means known to those of ordinary skill in the art. The order of addition of reactants or solvent does not affect the process. Reactants and/or solvent can be added sequentially or simultaneously in any suitable reaction vessel. For example, the metal hydroxide may be dissolved in alcohol and the resultant mixture added to the chloride quat or the chloride quat may be dissolved in alcohol and the metal hydroxide added to the resultant mixture. Importantly, the method of the present invention is suitable for commercial scale production techniques and equipment, yet convenient for small scale work.

Typically, the reactants and solvent will be stirred and heated to from about 20° C. to about 70° C. and held at that temperature for a period of from about 1 hours to about 5 hours. The reaction mixture is then cooled, first to room temperature and then to about 0° C. where it is held for about 1 hours to about 2 hours. Any precipitated metal chloride is collected as is known in the art, i.e. such as by filtration.

Alternatively, the reactants and solvent can be stirred at a slightly elevated temperature, i.e. from about 20° C. to about 40° C., to yield the hydroxy quat/solvent mixture. Hydroxy quat can be separated as above.

Di $C_8$–$C_{12}$ alkyl quaternary ammonium hydroxides, and particularly those prepared by the method of the present invention, can be formulated as metal-free wood preservative systems. These systems include biocidal effective amounts of at least one hydroxy quat and a suitable solvent, including aqueous and non-aqueous solvents. Preferably, the solvent is an aqueous solvent including, but not limited to, water, aqueous alcohol such as ethanol, ammonia water, and the like, or a combination of any of the foregoing.

Although other conventional additives may be added as required for application to different substrates and for different uses as known to those of ordinary skill in the art, metal stabilizers are not required and, in fact, are not recommended to inhibit leaching of the quat from the substrate. Accordingly, wood substrates, such as lumber, timber, or the like, can be treated with preservative systems which comprise the above hydroxy quat(s) diluted in a suitable solvent as above.

The amount of di $C_8$–$C_{12}$ alkyl quaternary ammonium hydroxide used to treat the substrate is a biocidal effective amount, i.e. that amount effective to inhibit the growth of or to kill one or more organism that causes wood rot, to inhibit sap staining, or any combination thereof. Such organisms include, but are not limited to, *Trametes viride* or *Trametes versicolor*, which cause a white rot; *Goeophyllium trabeum*, which causes a brown rot; and *Aspergillus niger*, which causes sap stain/mold.

Typically, a wood preservative system will comprise from about 0.1 to about 5 parts by weight of the hydroxy quat and from about 95 to about 99.9 parts by weight of solvent based upon 100 parts by weight of quat and solvent combined. Most preferably, the wood preservative system of the present invention will comprise from about 1 to about 2 parts by weight of hydroxy quat and from about 98 to about 99 parts by weight of solvent on the same basis.

Treatment of the substrate is accomplished by any means known to those of ordinary skill in the art including, but not limited to dipping, soaking, brushing, pressure treating or the like. The length of treatment required will vary according to treatment conditions, the selection of which are known to those skilled in the art.

The wood preservative systems of the present invention display greater resistance to leaching than wood preservatives currently used in the industry. Resistance to leaching is defined as retention of a biocidal effective amount, and preferably at least about 2% by weight, of hydroxy quat in the substrate over a prolonged period of at least about 100 hours and preferably about 350 hours. Applicants hypothesize, without being bound by any theory, that the hydroxide quat reacts or complexes with the woody matrix of the substrate, thereby "fixing" it in the substrate. It is also believed that the long chain hydroxy quats and the wood preservative systems that include such quats enhance waterproofing properties of the treated substrates.

DESCRIPTION OF THE PREFERRED EMBODIMENTS

The following examples illustrate the invention without limitation. All parts and percentages are given by weight unless otherwise indicated.

Quaternary compounds are quantified by two phase titration with sodium laurylsulfate and an indicator. The mixture is buffered to a pH of 10.

PREPARATION OF HYDROXY QUATS

EXAMPLE 1 —STOICHIOMETRIC AMOUNT OF METAL HYDROXIDE 180 grams (0.4 moles) of 80% didecyldimethylammonium chloride in 20% ethanol water (144 grams of DDAC), 180 ml of absolute denatured ethanol (denatured with methanol/isopropanol), and 26 grams (0.4 mole) of 85% potassium hydroxide pellets (22.1 grams of KOH) were mixed in a flask that was purged with nitrogen and equipped with a heating mantle and a magnetic stirrer. The mixture was stirred and heated at 60°–70° C. for three hours. The mixture was then allowed to cool to room temperature and finally cooled to 0° C. for at least one hour.

Potassium chloride precipitated, and the precipitate was collected on a vacuum filter. The solid was washed with cold ethanol and subsequently was dried, yielding 30 grams of dry potassium chloride. The quat solution was concentrated in a vacuum to about 75% active bases.

Yield was 180 grams of product containing 138 grams of didecyldimethylammonium hydroxide.

EXAMPLE 2

The procedure of Example 1 was followed, but the mixture was stirred mechanically at 50° C. for one hour. Potassium chloride precipitated, and the precipitate was collected on a vacuum filter. The solid was washed with cold ethanol and subsequently was dried, yielding 30 grams of dry potassium chloride.

Yield was 180 grams of product containing 138 grams of didecyldimethylammonium hydroxide.

EXAMPLE 3

0.022 mole of 8.5% potassium hydroxide pellets (1.23 grams of KOH) was added to 0.022 mole of 80% didecyldimethylammonium chloride in 20% ethanol/water (8 grams of DDAC) dissolved in 10 ml of ethanol. The resultant mixture was stirred and heated to 70° C. and held at this temperature for one-half hour. The pellets dissolved, and a fine precipitate formed. The mixture was then cooled and chilled to 0° C. The precipitated solid was collected on a filter and washed with cold ethanol. The filtrate was concentrated to yield a yellow/orange oil with a slight amine odor.

Results are summarized in Table 1.

COMPARATIVE EXAMPLE 3A

The procedure of Example 3 was followed substituting isopropanol for the ethanol.

Results are illustrated in Table 1.

EXAMPLE 4

0.022 mole of 85% potassium hydroxide pellets (1.23 grams of KOH) was added to 0.022 mole of 80% didecyldimethylammonium chloride in 20% ethanol/water (8 grams of DDAC) dissolved in 10 ml of propanol. The resultant mixture was stirred and heated to 80° C. and held at this temperature for one hour. The pellets dissolved, and a fine precipitate formed. The mixture was then cooled and chilled to 0° C. The precipitated solid was collected on a filter and washed with cold ethanol. The filtrate was concentrated to yield a yellow/orange oil with a slight amine odor.

Results are illustrated in Table 1.

EXAMPLE 5

The procedure of Example 3 was followed substituting sodium hydroxide for the potassium hydroxide.

Results are illustrated in Table 1.

COMPARATIVE EXAMPLE 5A

The procedure of Comparative Example 3 was followed substituting sodium hydroxide for the potassium hydroxide.

Results are illustrated in Table 1.

EXAMPLE 6

The procedure of Example 4 was followed substituting sodium hydroxide for the potassium hydroxide.

Results are illustrated in Table 1.

TABLE 1

| Preparation of Didecyldimethylammonium Hydroxide from Stoichiometric Amounts of Reactants | | | | | | |
|---|---|---|---|---|---|---|
| Example | 3 | 3A | 4 | 5 | 5A | 6 |
| Hydroxide | KOH | KOH | KOH | NaOH | NaOH | NaOH |
| Solvent | Ethanol | Isopropanol | n-propanol | Ethanol | Isopropyl | n-propanol |
| Conversion % | 96 | 86 | 95 | 81 | 66 | 83 |

Examples 3–6 when compared with Comparative Examples 3A and 5A demonstrate that the use of a normal $C_1$–$C_4$ alcohol as a reaction medium enhances conversion of the chloride quat to the hydroxy quat.

Furthermore, a comparison of examples 3 and 4 with Examples 5 and 6 illustrates the increase in conversion by the use of the preferred metal hydroxide, potassium hydroxide.

EXAMPLE 7

The procedure of Example 3 was followed, but the mixture was heated to 25° C. and held for one hour. Results are illustrated in Table 2.

EXAMPLE 8

The procedure of Example 3 was followed, but the mixture was heated to 60° C. and held for 0.6 hour. Results are illustrated in Table 2.

EXAMPLE 9

The procedure of Example 3 was followed, but the mixture was heated to 90° C. and held for 0.3 hour. Results are illustrated in Table 2.

EXAMPLE 10

The procedure of Example 5 was followed, but the mixture was heated to 25° C. for 3.5 hours. Results are illustrated in Table 2.

EXAMPLE 11

The procedure of Example 5 was followed, but the mixture was heated to 60° C. for 1.5 hours. Results are illustrated in Table 2.

EXAMPLE 12

The procedure of Example 5 was followed, but the mixture was heated to 90° C. for 1 hour. Results are illustrated in Table 2.

TABLE 2

| | Temperature and Time of Reaction | | | | | |
|---|---|---|---|---|---|---|
| | 7 | 8 | 9 | 10 | 11 | 12 |
| Hydroxide | KOH | KOH | KOH | NaOH | NaOH | NaOH |
| Temperature (°C.) | 25 | 60 | 90 | 25 | 60 | 90 |
| Time (Hours) | 1 | 0.6 | 0.3 | 3.5 | 1.5 | 1 |
| Conversion (%) | 91 | 92 | 93 | 79 | 81 | 85 |

Examples 7–12 illustrate the effects of reaction temperatures and time on conversion of chloride quat to hydroxy quat.

EXAMPLE 13

The procedure of Example 1 is followed substituting 0.4 moles of 80% octyldecyldimethylammonium chloride for the didecyldimethylammonium chloride to yield octyldecyldimethylammonium hydroxide.

EXAMPLE 14

The procedure of Example 1 is followed substituting 0.4 moles of 80% iso-nonyldecyldimethylammonium chloride for the didecyldimethylammonium chloride to yield iso-nonyldecyldimethylammonium hydroxide.

EXAMPLE 15

The procedure of Example 1 is followed substituting 0.4 moles of 80% benzyldodecyldimethylammonium chloride for the didecyldimethylammonium chloride to yield benzyldodecyldimethylammonium hydroxide.

EXAMPLE 16

The procedure of Example 1 is followed substituting 0.4 moles of an 80% mixture of benzyldodecyl-; benzyltetradecyl-; and benzylhexadecyldimethylammonium chloride for the didecyldimethylammonium chloride to yield a mixture of benzyldodecyl-; benzyltetradecyl-; and benzylhexadecyldimethylammonium hydroxide.

EXAMPLE 17

The procedure of Example 1 is followed substituting 0.4 moles of 80% dihexadecyldimethylammonium chloride for the didecyldimethylammonium chloride to yield dihexadecyldimethylammonium hydroxide.

EXAMPLE 18

The procedure of Example 1 is followed substituting 0.4 moles of 80% dodecyltrimethylammonium chloride for the didecyldimethylammonium chloride to yield dodecyltrimethylammonium hydroxide.

STOICHIOMETRIC EXCESS OF METAL HYDROXIDE

EXAMPLE 19

A nitrogen purged reactor equipped with a heating mantle and a magnetic stir bar was charged with 0.4 mole of 80% didecyldimethylammonium chloride (144 grams of DDAC) in 20% ethanol/water, 180 ml of ethanol, and 0.49 mole of 85% potassium hydroxide (27.5 grams of KOH) pellets. The mixture was heated at 60°–70° C. for 3 hours, allowed to cool to room temperature, and then cooled to 0° C. for about one hour to precipitate potassium chloride. The precipitate was collected on a vacuum filter, and the solid was washed with cold ethanol. Potassium chloride yield was 30.8 grams.

The supernatant solution, which contained the hydroxy quat and 0.09 moles of excess potassium hydroxide, was stirred with 2 grams (0,045 moles) of carbon dioxide gas (from dry ice). The mixture was kept cold for an hour and then was vacuum filtered to remove 7.2 grams (theoretical 6.2 grams) of potassium carbonate.

Conversion percentage to the hydroxy quat was determined to be 99%.

TREATMENT OF WOOD SUBSTRATES

EXAMPLE 20

End grain pine wafers were weighed and then soaked with didecyldimethylammonium hydroxide until a weight gain of 30% was observed.

The treated wafers were then placed in water and weighed periodically to determine resistance to leaching.

Results are illustrated in FIGS. 1A and 1B.

COMPARATIVE EXAMPLE 20A

The procedure of Example 20 was followed substituting didecyldimethylammonium chloride for the didecyldimethylammonium hydroxide.

Results are illustrated in FIGS. 1A and 1B.

FIGS. 1A and 1B illustrate that the hydroxy quat resists leaching for extended periods while the chloride quat leaches to levels of 1% or less in a relatively short period.

EXAMPLE 21

A 10"×0.5"×0.75" piece of ponderosa pine was equilibrated, weighed, and heated for two hours at 60° C. The wood was treated with a treating solution of 2% didecyldimethylammonium hydroxide in water by heating in the solution at 60° C. to 80° C. for one hour, cooling and standing overnight, and then being subjected to a second warm to cool cycle. The samples were allowed to dry to constant weight, and the uptake was determined by comparing starting and finishing weights.

The samples were then heated for two hours at 60° C., and the weight of the warm treated samples was compared to the over dried sticks before treatment.

Results are illustrated in Table 3.

COMPARATIVE EXAMPLE 21A

The procedure of Example 21 was followed, omitting the didecyldimethylammonium hydroxide from the treating solution.

COMPARATIVE EXAMPLE 21B

The procedure of Example 21 was followed, substituting didecyldimethylammonium chloride for the didecyldimethylammonium hydroxide.

Results are illustrated in Table 3.

EXAMPLE 22

The procedure of Example 21 was followed substituting a solution of 1% didecyldimethylammonium hydroxide in 3% ammonia water for the solution of the 2% didecyldimethylammonium hydroxide in water.

Results are illustrated in Table 3.

COMPARATIVE EXAMPLE 22A

The procedure of Example 22 was followed, omitting the didecydimethylammonium hydroxide from the treating solution.

Results are illustrated in Table 3.

COMPARATIVE EXAMPLE 22B

The procedure of Example 22 was followed, substituting didecyldimethylammonium chloride for the didecyldimethylammonium hydroxide.

Results are illustrated in Table 3.

EXAMPLE 23

A piece of wood was treated according to the procedure of Example 21. The piece of wood was then soaked in water at room temperature for 24 hours, dried to constant weight, and weighed to determine how much chemical remained. The piece of wood was soaked for 96 additional hours (120 hours total), dried to constant weight, and weighed to determine the leaching of quat from the treated wood. The water was changed several times during this period.

Results are illustrated in Table 4.

COMPARATIVE EXAMPLE 23A

A piece of wood was treated according to the procedure of Comparative Example 21A.. The piece of wood was then soaked according to the procedure of Example 23.

Results are illustrated in Table 4.

COMPARATIVE EXAMPLE 23B

A piece of wood was treated according to the procedure of Comparative Example 21B. The piece of wood was then soaked according to the procedure of Example 23.

Results are illustrated in Table 4.

EXAMPLE 24

A piece of wood was treated according to the procedure of Example 22. The piece of wood was then soaked according to the procedure of Example 23.

Results are illustrated in Table 4.

COMPARATIVE EXAMPLE 24A

A piece of wood was treated according to the procedure of Comparative Example 22A. The piece of wood was then soaked according to the procedure of Example 23.

Results are illustrated in Table 4.

COMPARATIVE EXAMPLE 24B

A piece of wood was treated according to the procedure of Comparative Example 22B. The piece of wood was then soaked according to the procedure of Example 23.

Results are illustrated in Table 4.

TABLE 3

| | Weight Uptake from Quat Solutions | | | | | |
|---|---|---|---|---|---|---|
| Example | 21 | 21A | 21B | 22 | 22A | 22B |
| Solvent | Water | Water | Water | 3% Ammonia | 3% Ammonia | 3% Ammonia |
| Quat | Hydroxide | — | Chloride | Hydroxide | — | Chloride |
| Weight Uptake (%) | 2.5 | −0.4 | 0.6 | 1.6 | −0.6 | 2.0 |

Examples 21 and 22, when compared with Comparative Examples 21A, 21B, 22A, and 22B respectively, illustrate the ability of the hydroxy quats prepared according to the present invention to be applied to wood substrates. The hydroxy quat is absorbed better than the chloride quat in water, and is absorbed similarly to the art accepted chloride quat in ammonia/water. However, the hydroxy quats can be used without metal coupling agents in treating wood substrates.

TABLE 4

| | Leaching of Quat | | | | | |
|---|---|---|---|---|---|---|
| Example | 23 | 23A | 23B | 24 | 24A | 24B |
| Solvent | Water | Water | Water | 3% Ammonia | 3% Ammonia | 3% Ammonia |
| Quat | Hydroxide | | Chloride | Hydroxide | | Chloride |
| Weight Uptake (%) | 2.5 | 0.4 | 0.6 | 1.6 | 0.6 | 2.0 |
| Retained Quat at 24 Hours (Absolute %/Relative %) | 2.3/92 | −0.2/— | 0.5/83 | 1.8/110 | −0.3/— | 1.7/85 |
| Retained Quat at 120 Hours (Absolute %/Relative | 1.8/72 | −0.2/— | 0.4/67 | 1.3/81 | −0.3/— | 1.3/65 |

TABLE 4-continued

| | Leaching of Quat | | | | | |
|---|---|---|---|---|---|---|
| Example | 23 | 23A | 23B | 24 | 24A | 24B |
| %) | | | | | | |

Example 23, when compared with Comparative Examples 23A and 23B, and Example 24, when compared with Comparative Examples 24A and 24B, demonstrate the improved retention properties of hydroxy quats prepared according to the present invention over conventional chloride quats, particularly in the absence of metal stabilizers.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

I claim:

1. A method for the preparation of $C_1$-$C_{20}$ alkyl or aryl-substituted alkyl, $C_8$-$C_{20}$ alkyl quaternary ammonium hydroxide, said method comprising
   (a) reacting a $C_1$-$C_{20}$ alkyl or aryl-substituted alkyl, $C_8$-$C_{20}$ alkyl quaternary ammonium chloride reactant and a metal hydroxide reactant in a solvent comprising a $C_1$-$C_4$ normal alcohol, said metal hydroxide being present in an amount sufficient to yield said $C_1$-$C_{20}$ alkyl or aryl-substituted alkyl, $C_8$-$C_{20}$ alkyl quaternary ammonium hydroxide; and
   (b) removing any excess metal hydroxide by reacting with carbon dioxide.

2. A method as defined in claim 1 wherein said $C_1$-$C_{20}$ alkyl or aryl-substituted alkyl is selected from the group consisting of a methyl, $C_8$ alkyl, $C_9$ isoalkyl, $C_{10}$ alkyl, $C_{12}$ alkyl, $C_{14}$ alkyl, $C_{16}$ alkyl, and benzyl group, and said $C_8$-$C_{20}$ alkyl group is selected from the group consisting of a $C_{10}$ alkyl, $C_{12}$ alkyl, $C_{14}$ alkyl, and $C_{16}$ alkyl group.

3. A method for the preparation of di $C_8$-$C_{12}$ alkyl quaternary ammonium hydroxide, said method comprising
   (a) reacting a di $C_8$-$C_{12}$ alkyl quaternary ammonium chloride reactant and a metal hydroxide reactant in a solvent comprising a $C_1$-$C_4$ normal alcohol, said metal hydroxide being present in an amount sufficient to yield said di $C_8$-$C_{12}$ alkyl quaternary ammonium hydroxide.

4. A method as defined in claim 3 wherein said di $C_8$-$C_{12}$ alkyl quaternary ammonium hydroxide comprises didecyldimethylammonium hydroxide and wherein said di $C_8$-$C_{12}$ alkyl quaternary ammonium chloride comprises didecyldimethylammonium chloride.

5. A method as defined in claim 3 wherein said metal hydroxide comprises potassium hydroxide.

6. A method as defined in claim 3 wherein said $C_1$-$C_4$ normal alcohol comprises ethanol.

7. A method as defined in claim 3 wherein said di $C_8$-$C_{12}$ alkyl quaternary ammonium hydroxide comprises didecyldimethylammonium hydroxide, said di $C_8$-$C_{12}$ quaternary ammonium chloride comprises didecyldimethylammonium chloride, and said $C_1$-$C_4$ normal alcohol comprises ethanol.

8. A method as defined in claim 5 wherein said amount of potassium hydroxide is a stoichiometric amount with respect to said didecyldimethylammonium chloride.

9. A method as defined in claim 5 wherein said amount of potassium hydroxide is a stoichiometric excess with respect to said didecyldimethylammonium chloride.

10. A method as defined in claim 9 wherein said excess ranges from about 2% to about 20% over a stoichiometric amount.

11. A method for the preparation of didecyldimethylammonium hydroxide, said method comprising
    (a) reacting didecyldimethylammonium chloride and potassium hydroxide in ethanol, said potassium hydroxide being present in at least a stoichiometric amount with respect to said didecyldimethylammonium chloride; and
    (b) removing any excess metal hydroxide by reacting with carbon dioxide.

12. A method as defined in claim 1 wherein said $C_1$-$C_4$ normal alcohol is selected from the group consisting of ethanol, n-propanol, and a combination thereof.

13. A method for the preparation of $C_1$-$C_{20}$ alkyl or aryl-substituted alkyl, $C_8$-$C_{20}$ alkyl quaternary ammonium hydroxide, said method comprising
    (a) reacting a $C_1$-$C_{20}$ alkyl or aryl-substituted alkyl, $C_8$-$C_{20}$ alkyl quaternary ammonium chloride reactant and a metal hydroxide reactant in a solvent comprising a $C_1$-$C_4$ normal alcohol, said metal hydroxide being present in an amount sufficient to yield said $C_1$-$C_{20}$ alkyl or aryl-substituted alkyl, $C_8$-$C_{20}$ alkyl quaternary ammonium hydroxide wherein the weight ratio of quaternary ammonium chloride to solvent is about 1.1:1; and
    (b) removing any excess metal hydroxide by reacting with carbon dioxide.

14. A method for the preparation of $C_1$-$C_{20}$ alkyl or aryl-substituted alkyl, $C_8$-$C_{20}$ alkyl quaternary ammonium hydroxide, said method comprising
    (a) reacting a $C_1$-$C_{20}$ alkyl or aryl-substituted alkyl, $C_8$-$C_{20}$ alkyl quaternary ammonium chloride reactant and a stoichiometric amount of potassium hydroxide in a solvent comprising a $C_1$-$C_4$ normal alcohol, to yield said $C_1$-$C_{20}$ alkyl or aryl-substituted alkyl, $C_8$-$C_{20}$ alkyl quaternary ammonium hydroxide; and
    (b) removing any excess potassium hydroxide by reacting with carbon dioxide.

15. A method for the preparation of $C_1$-$C_{20}$ alkyl or aryl-substituted alkyl, $C_8$-$C_{20}$ alkyl quaternary ammonium hydroxide, said method comprising
    (a) reacting a $C_1$-$C_{20}$ alkyl or aryl-substituted alkyl, $C_8$-$C_{20}$ alkyl quaternary ammonium chloride reactant and potassium hydroxide reactant in a solvent comprising an aqueous $C_1$-$C_4$ normal alcohol, said potassium hydroxide being present in an amount sufficient to yield said $C_1$-$C_{20}$ alkyl or aryl-substituted alkyl, $C_8$-$C_{20}$ alkyl quaternary ammonium hydroxide; and
    (b) removing any excess potassium hydroxide by reacting with carbon dioxide.

* * * * *